United States Patent
Belinsky et al.

(10) Patent No.: US 11,266,599 B2
(45) Date of Patent: Mar. 8, 2022

(54) INHALABLE DRY POWDER CYTIDINE ANALOGUE COMPOSITION AND METHOD OF USE AS A TREATMENT FOR CANCER

(71) Applicant: Lovelace Biomedical Research Institute, Albuquerque, NM (US)

(72) Inventors: Steven A. Belinsky, Albuquerque, NM (US); Philip J. Kuehl, Albuquerque, NM (US); Aaron Badenoch, Bend, OR (US); Michael Burke, Bend, OR (US); Devon Dubose, Bend, OR (US)

(73) Assignee: Lovelace Biomedical Research Institute, Albuquerque, NM (US)

( * ) Notice: Subject to any disclaimer, the term of this patent is extended or adjusted under 35 U.S.C. 154(b) by 0 days.

(21) Appl. No.: 16/988,312

(22) Filed: Aug. 7, 2020

(65) Prior Publication Data

US 2020/0368157 A1    Nov. 26, 2020

Related U.S. Application Data

(63) Continuation of application No. PCT/US2019/017083, filed on Feb. 7, 2019.
(Continued)

(51) Int. Cl.
*A61K 9/00* (2006.01)
*A61K 9/12* (2006.01)
(Continued)

(52) U.S. Cl.
CPC .............. *A61K 9/0075* (2013.01); *A61K 9/12* (2013.01); *A61K 31/7068* (2013.01);
(Continued)

(58) Field of Classification Search
None
See application file for complete search history.

(56) References Cited

U.S. PATENT DOCUMENTS 6,582,728 B1    6/2003    Platz et al.
8,410,136 B2    4/2013    Zeldis
(Continued)

FOREIGN PATENT DOCUMENTS

CN      102485232 A    6/2012
WO    2010093435 A1    8/2010
(Continued)

OTHER PUBLICATIONS

"International Search Report dated Jun. 7, 2019 for PCT/US2019/017083", dated Jun. 7, 2019.
(Continued)

*Primary Examiner* — Melissa S Mercier
(74) *Attorney, Agent, or Firm* — Peacock Law P.C.; Janeen Vilven

(57) ABSTRACT

An embodiment of the present invention provides for a dry powder pharmaceutical composition suitable for dispersion in an aerosol for inhaled administration to a patient with cancer, the composition comprising: a cytidine analogue including salts, solvates, hydrates, and esters thereof; and a pharmaceutically acceptable excipient together forming the dry powder pharmaceutical composition suitable for dispersion in the aerosol for administration via inhalation to the patient with cancer. Another embodiment provides for a method of making the composition and a further embodiment provides for a method a treating a patient in need thereof with the composition.

33 Claims, 5 Drawing Sheets

Cytidine

5-Azacytidine

Related U.S. Application Data

(60) Provisional application No. 62/627,428, filed on Feb. 7, 2018.

(51) Int. Cl.
   A61K 31/7068 (2006.01)
   A61K 47/26 (2006.01)
   A61K 47/10 (2017.01)
   A61K 47/18 (2017.01)

(52) U.S. Cl.
   CPC ............ *A61K 47/10* (2013.01); *A61K 47/183* (2013.01); *A61K 47/26* (2013.01)

(56) References Cited

U.S. PATENT DOCUMENTS

| | | | |
|---|---|---|---|
| 8,623,384 | B2 | 1/2014 | Zeldis |
| 8,841,277 | B2 | 9/2014 | Nguyen et al. |
| 9,056,120 | B2 | 6/2015 | Zeldis |
| 9,375,443 | B2 | 6/2016 | Xu et al. |
| 9,951,098 | B2 | 4/2018 | Rajendiran et al. |
| 10,022,303 | B2 | 7/2018 | Bosch et al. |
| 2004/0092470 | A1 | 5/2004 | Leonard et al. |
| 2013/0274219 | A1* | 10/2013 | Nguyen .................. A61P 43/00 514/43 |
| 2016/0338959 | A1 | 11/2016 | Troiano |

FOREIGN PATENT DOCUMENTS

| | | |
|---|---|---|
| WO | 2013033176 A1 | 3/2013 |
| WO | 2013126636 A1 | 8/2013 |

OTHER PUBLICATIONS

Balouzet, C. , et al., "Stability of 25 mg/ml azacitidine suspensions kept in fridge after freezing", Phamr Technol Hosp Pharm, vol. 2, 2017, 11-16.

Belinsky, S. A., et al., "Combination therapy with vidaza and entinostat suppresses tumor growth and reprograms the epigenome in an orthotopic lung cancer model", Cancer Res, vol. 71, 2011, 454-462.

Cameron, E. E., et al., "Synergy of demethylation and histone deacetylase inhibition in the re-expression of genes silenced in cancer", Nat Genet, vol. 21, 1999, 103-107.

Carbone, D. P., et al., "First-line nivolumab in stage IV or recurrent non-small cell lung cancer", N Eng J Med, vol. 376, 2017, 2415-2426.

Chen, Z., et al., "Non-small cell lung cancers: a heterogenous set of diseases", Nat Rev Cancer, vol. 14, 2014, 535-556.

Gad, S. C., et al., "Nonclinical vehicle use in studies by multiple routes in multiple species", Int J Toxc., vol. 25, 2006, 499-521.

Garcia-Manero, G. , et al., "Phase I study of oral azacitidine in myelodysplastic syndromes, chronic myelomonocytic leukemia and acute myeloid leukemia", J Clin Oncol, vol. 29, 2011, 2521-2527.

Hamishehehkar, H. , et al., "The role of carrier in dry powder inhaler", Recent Advances in Novel Drug Carrier Systems, Sezer, Ali Demir, ed., InTech, 2012, 39-66.

Herman, J. G., et al., "Gene silencing in cancer in association with promoter hypermethylation", N Eng J Med, vol. 349, 2003, 2042-2054.

Ho, D. H., et al., "Clinical pharmacology of 1-beta-darabinofuranosyl cytosine", Clin Pharmacol Ther, vol. 12, 1971, 944-954.

Jones, P. A., et al., "The fundamental role of epigenetic events in cancer", Nat Rev Genet, vol. 3, 2002, 415-428.

Juergens, R. A., et al., "Combination epigenetic therapy has efficacy in patients with refractory advanced non-small cell lung cancer", Cancer Discovery, vol. 1, 2011, 598-607.

Kantarjian, H. M., et al., "Guadecitabine (SGT-110) in treatment-naive patients with acute myeloid leukaemia phase 2 results from a multicentre, randomised phase 1/2 trial", Lancet Oncol., vol. 18, 2017, 1317-1326.

Lechuga-Ballesteros, D. , et al., "Trileucine improves aerosol performance and stability of spray-dried powders for inhalation", J Pharmac Sci., vol. 97, 2008, 287-302.

March, T. H., et al., "Refinement of an orthotopic lung cancer model in the nude rat", Vet Pathol, vol. 38, 2001, 483-490.

Meng, X. , et al., "PD-1/PD-L1 checkpont blockages in non-small cell lung cancer", Lancet Oncol, vol. 12, 2011, 175-180.

Momparler, Richard L., "A Perspective on the Comparative Antileukemic Activity of 5-Aza-2'-deoxycytidine (Decitabine) and 5-Azacytidine (Vidaza)", Pharmaceuticals, vol. 5, 2012, 875-881.

Nakamura, K. , et al., "DNA methyltransferase inhibitor zebularine induces human cholangiocarcinoma cell death through alteration of DNA methylation status", PLOS One, vol. 10:e0120545, 2015.

Pao, W. , et al., "New driver mutations in non-small lung cancer", Lancet Oncol, vol. 12, 2011, 175-180.

Qiu, X. , et al., "Aerosol azacytidine inhibits orthotopic lung cancers in mice through its DNA demethylation and gene reactivation effects", PLoS One, vol. 9:e109874, 2014.

Qiu, X. , et al., "Toxicity and pharmacokinetic studies of aerosolized clinical grade azacytidine", Clin Lung Cancer, vol. 17, 2016, 214-222.

Reed, M. D., et al., "Aerosolized 5-azacytidine suppresses tumor growth and reprograms the epigenome in an orthotopic lung cancer model", Br J. Cancer, vol. 109, 2013, 1775-1781.

Savona, M. R., et al., "Extended dosing with CC-486 (oral azacitidine) in patients with myeloid malignancies", Am J Hematol., vol. 93, 2018, 1199-1206.

Siegel, R. L., et al., "Cancer statistics", CA Cancer J Clin, vol. 67, 2017, 7-30.

Silverman, L. R., et al., "Randomized controlled trial of azacitidine in patients with the myelodysplastic syndrome: a study of the cancer and leukemia group", J Clin Oncol, vol. 20, 2002, 2429-2440.

The Cancer Genome Atlas Research, Network , "Comprehensive genomic characterization of squamous cell lung cancers", Nature, vol. 489, 2012, 519-525.

The Cancer Genome Atlas Research, Network , "Comprehensive molecular profiling of l ung adenocarcinoma", Nature, vol. 511, 2014, 543-550.

Wakelle, H. A., et al., "Adjuvant chemotherapy with or without bevacizumab in patients with resected non-small lung cancer (D1505): an open-label, multicenter, randomized, phase 3 trial", Lancet Oncol, vol. 18, 2017, 1610-1623.

Wikipedia, "cmax (pharmacology)", https://en.wikipedia.org/w/index.php?title=Cmax_(pharmacology)&oldid=794759788, retrieved Apr. 2, 2019, Aug. 9, 2017.

Wrangle, J. , et al., "Alterations of immune response of non-small cell lung cancer with azacytidine", Oncotarget, vol. 4, 2013, 2067-2079.

Yang, A. S., et al., "DNA methylation changes after 5-aza-2'-deoxycytidine therapy in patients with leukemia", Cancer Res, vol. 66, 2006, 5495-5503.

Tiefenbacher, Alfred E (GMBH & CO KG) and Project Pharmaceutics GMBH: "Optimized Lyphophilization of Azacitidine", Reseach Disclosure, Kenneth Mason Publications, Hampshire, UK, GB, vol. 596, No. 15, Dec. 1, 2013, p. 2.

\* cited by examiner

Cytidine

5-Azacytidine

Zebularine

5-Aza-2'-deoxyazacytidine

SG-110

```
┌─────────────────────────┐
│      5 AZA powder       │
└─────────────────────────┘
            │
            ▼
┌─────────────────────────┐      ┌──────────────────────────┐
│ Add 10% DMSO to solubilize │      │ Solubilize excipients such │
│      5 AZA powder        │      │ as trehalose and leucine in│
└─────────────────────────┘      │           H₂O            │
            │                    └──────────────────────────┘
            ▼                                   │
┌─────────────────────────────────────────┐     │
│        In-line mixing of DMSO-          │◄────┘
│  5 AZA and excipients just prior        │
│           to atomization                │
└─────────────────────────────────────────┘
            │
            ▼
┌─────────────────────────────────────────┐
│    Droplets evaporate forming dry       │
│              powder of                  │
│    Trehalose/leucine/5 AZA with         │
│    residual DMSO having MMDA of         │
│           between 1-5 μm                │
└─────────────────────────────────────────┘
```

FIG. 4

INHALABLE DRY POWDER CYTIDINE ANALOGUE COMPOSITION AND METHOD OF USE AS A TREATMENT FOR CANCER

CROSS-REFERENCE TO RELATED APPLICATIONS

This application is a continuation application of International Patent Application No. PCT/US2019/017083, entitled "Inhalable Dry Powder Cytidine Analogue Composition and Method of Use as a Treatment for Cancer", filed Feb. 7, 2019, which claims priority to and the benefit of the filing of U.S. Provisional Patent Application No. 62/627,428, entitled "Inhalable dry powder 5-azacytidine for treatment and prevention of lung cancer", filed on Feb. 7, 2018, and the specification and claims thereof are incorporated herein by reference.

STATEMENT REGARDING FEDERALLY SPONSORED RESEARCH OR DEVELOPMENT

This invention was made with government support under Grant No. R01 CA196590 awarded by National Institutes of Health/National Cancer Institute. The government has certain rights in the invention.

THE NAMES OF PARTIES TO A JOINT RESEARCH AGREEMENT

Not Applicable.

INCORPORATION BY REFERENCE OF MATERIAL SUBMITTED ON A COMPACT DISC

Not Applicable.

STATEMENT REGARDING PRIOR DISCLOSURES BY THE INVENTOR OR A JOINT INVENTOR

Not Applicable

COPYRIGHTED MATERIAL

Not Applicable.

BACKGROUND OF THE INVENTION

Field of the Invention (Technical Field)

Lung cancer with 220,000 new cases diagnosed annually in the United States remains the leading cause of cancer-related deaths (1,2). Novel targeted- and chemo-therapies for lung cancer (LC) has achieved modest improvement in median survival that is now approximately 6.5 months for advanced LC, but they offer no clear path to treatments that could make this a chronic, rather than fatal disease. A major recent advance in LC is the integration of immune checkpoint inhibitors to the treatment paradigm; however only ~20% of NSCLC patients derive durable benefit from this treatment (3-5). Even for the 15% of lung cancers for which curative intent surgery is performed, 40% of cases recur within five years and there is no effective adjuvant therapy for this population. Thus, there is a clear need for new highly efficacious therapies that can treat local and metastatic lung cancer with low systemic toxicity. In addition, therapies that can be extended chronically to maintain disease status through progression free survival and prevent cancer recurrence would be a paradigm shift in the management of this fatal disease through dramatically increasing overall survival.

Epigenetics refers to the study of long-term changes in gene expression, which may or may not be heritable, and are not caused by changes to the DNA sequence (6). Epigenetic mechanisms involve DNA methylation and histone modifications. In DNA methylation, a cytosine residue that is followed by a guanine residue (CpG) becomes methylated through a process in which the DNA methyltransferase (DNA MTase) family of enzymes catalyzes the transfer of a methyl group to DNA that in turn affects that section of the chromatin and represses the expression of the affected genes (7). The second category is histone modifications. Histones are proteins that are involved in the folding and compaction of the chromatin and deacetylation of histones and methylation of lysine moieties on the histone tails also leads to changes in chromatin conformation that blocks transcription of the affected genes. Unlike genetic mutations, epigenetics is reversible through pharmacological inhibitors. 5-Azacitidine ([5AZA], for example Vidaza®) and 5-aza-2'-deoxyazacytidine ([DAC], for example Decitabine®) are derivatives/analogues of the naturally occurring nucleoside cytidine (FIG. 1). Cytidine is present in DNA and RNA and when the DNA MTase is inhibited, hypomethylation of DNA and gene re-expression can occur (6). Additional chemical analogs of cytosine that were evaluated as therapeutics include zebularine and SG-110 (for example Guadecitabine®) (8, 9).

Epigenetic therapy through its ability to activate these genes offers a strategy that could ultimately produce durable and sustained tumor regression. Cytosine methylation appears dominant in transcriptional repression. However, while inhibitors of histone deacetylation (HDACi) are not very effective in inducing re-expression of genes silenced by promoter hypermethylation, such inhibitors can synergize with demethylating agents to relieve transcriptional repression (10). 5AZA and/or DAC delivered in liquid formulations through reconstitution in sterile water have been proven as a potent therapy for myelodysplasia with an overall response rate (ORR) of >60%, leading to FDA approval for the treatment of these diseases (11, 12).

The Cancer Genome Atlas (TCGA) has interrogated over 800 NSCLCs using the Illumina Methylation 450 Beadchip (HM450K) and revealed that virtually all tumors contain hundreds of genes that have densely cytosine methylated promoter regions associated with reduced transcription (13, 14). Thus, epigenetic therapy could offer an approach to affect the growth of lung tumors. A Phase I/II trial in which heavily pretreated LC patients that had received three prior lines of chemotherapy (a setting where response rates are usually ~10%) were treated with 5AZA and the HDACi entinostat. This therapy was well tolerated, 10 of 34 evaluable patients had stable disease (29%) with one partial, and one complete response for an ORR of 5.8% (15).

An additional utility of epigenetic therapy that is emerging is the "priming" of tumors for subsequent therapies, most notably immune-checkpoint blockers targeting programmed death 1 protein [PD-L1]. 5AZA administered in vitro increased the expression of PD-L1 in LC cell lines, which may shift the balance between immune activation and inhibition, a hypothesis that is being tested in clinical trials using epigenetic priming (systemic dosing) followed by the anti-PD-L1 antibody Nivolumab (16).

The expansion of epigenetic therapy and improvement of ORR into Phase III trials or to adjuvant therapy is constrained by required continuous daily subcutaneous dosing schedule and the poor pharmacokinetic (PK) properties of 5AZA for distribution to the lung and tissues where metastatic disease often occurs (brain and liver). 5AZA and DAC are relatively unstable in aqueous solution at room temperature and are subject to hydrolysis and catabolism by cytidine deaminase whose expression is the highest in the liver, thereby reducing the concentration of drug after subcutaneous or intravenous administration prior to reaching the lung (17). An oral formulation of 5AZA is also a substrate for cytidine deamination by cytidine deaminase (CDA), and toxicity in the GI tract has limited the delivered dose in conjunction with a large drug dilution effect seen with other orally delivered drugs prior to reaching the lungs (18, 19). Cumulative exposure to maximum tolerated oral doses of 300 mg 5AZA per day 21 days provides only 57% of the exposure seen with injectable 5AZA (75 mg/m2) for 7 days per 28-day cycle (19). However, with the 300 mg daily dose of 5AZA delivered orally, 84% of patients had gastrointestinal toxicity compare to 25% of patients receiving injectable 5AZA (19). These barriers could be mitigated by inhaled delivery that achieves high local tissue concentrations to achieve maximum clinical effects while minimizing systemic toxicities. This should greatly benefit patients with localized unresectable disease that includes bronchoalveolar carcinoma (BAC [~25,000 cases/yr]) and stage III adenocarcinoma (AdC) or squamous cell carcinoma (SCC [~50,000 cases/yr]), where inhaled delivery of 5AZA in the presence or absence of additional drugs (e.g. anticancer agents) for example those that target heterochromatin, could be very effective against these cancers.

BRIEF SUMMARY OF THE INVENTION

According to one embodiment of the present invention, a dry powder pharmaceutical composition suitable for dispersion in an aerosol for inhaled administration to a patent with cancer is provided. The composition comprising a cytidine analogue including salts, solvates, hydrates, and esters thereof; and a pharmaceutically acceptable excipient together forming the dry powder pharmaceutical composition suitable for dispersion in the aerosol for administration via inhalation to the patent with cancer. In one example, the excipient is an amino acid selected from the group consisting of: leucine, trileucine, isoleucine or any combination thereof but not limited thereto. In another example, the excipient is a sugar or alcohol. For example, the sugar or alcohol is selected from the group consisting of trehalose, lactose, mannitol, sorbitol, raffinose, inositol and erythritol. In a further example, the excipient comprises trehalose and/or leucine. The cytidine analogue may be selected from the group consisting of: 5-azacytidine, zebularine, 5-Aza-2'-deoxycitidine, SG-110 and the salts, solvates, hydrates, and esters thereof. In one embodiment, the pharmaceutical excipient is from about 99%-1% by weight of the dry powder and wherein the cytidine analogue including salts, solvates, hydrates, and esters thereof is from about 1-99% by weight of the dry powder with between about 0-20% residual DMSO. Further, the residual DMSO may be between about 5-15% DMSO. For example, the composition may comprise trehalose in the range of between about 0-99% w/w; leucine in the range of between 0-99% w/w; cytidine analogue including salts, solvates, hydrates, and esters thereof in the range from about 0.1-50%; and a residual of DMSO between 0.1-20% residual DMSO. In one embodiment, the composition is formed from atomization of the cytidine analogue in a solution of DMSO. In another embodiment, the dry powder has a MMAD of between about 1-5 µm.

Another embodiment of the present invention provides a method of forming a dry powder composition comprising a cytidine analogue including salts, solvates, hydrates and esters thereof comprising the steps of dissolving the cytidine analogue in DMSO to form a cytidine analogue DMSO solution. A pharmaceutically acceptable excipient is dissolved in a solvent. The cytidine analogue is combined with a DMSO solution and the dissolved excipient via mixing. Droplets are formed via atomization. The droplets are evaporatively dried to form particles comprising cytidine analogue having an MMAD of between about 1-5 µm. For example, the excipient may comprise an amino acid and/or sugar. The amino acid may be selected from the group consisting of: leucine, trileucine and isoleucine but not limited thereto. The sugar can be selected from the group consisting of: hexahydric alcohols, and sugar alcohols that include, but are not limited to trehalose, lactose, mannitol, sorbitol, raffinose, inositol and erythritol. In one embodiment, the excipient comprises trehalose and/or leucine. In another embodiment, the dry powder comprises residual DMSO. The mixing may be by in-line mixing. The cytidine analogue may be selected from the group consisting of: 5-azacytidine, zebularine, 5-Aza-2'-deoxycitidine, SG-110 and salts, solvates, hydrates, and esters thereof. In one embodiment the excipient is from about 99%-1% by weight of the dry powder and wherein the cytidine analogue including salts, solvates, hydrates, and esters thereof is from about 1-99% by weight of the dry powder with between about 0-20% residual DMSO. The residual DMSO is between about 5-15% DMSO. In one embodiment of the method, the dry powder composition comprises: trehalose in the range of between about 0-99% w/w; leucine in the range of between 0-99% w/w; cytidine analogue including salts, solvates, hydrates, and esters thereof in the range from about 0.1-50%; and a residual of DMSO between 0.1-20% residual DMSO. For example, the composition is formed from atomization of the cytidine analogue in a solution of DMSO. In one embodiment, the dry powder composition has a MMAD of between about 1-5 µm.

Another embodiment of the present invention provides a method of treating cancer in a subject. The method comprises pulmonary administering to a subject in need thereof a physiologically effective amount of a dispersible pharmaceutical-based dry powder composition as described herein. The cancer may be located in the lung or the cancer can be located outside of the lung. The method may include delivering a therapeutically effective dose of a cytidine analogue compound including salts, solvates, hydrates and esters thereof to the lung of the subject by inhalation of a dispersion formed by aerosolization of a dry powder formulation comprising the cytidine analogue compound at a concentration from about 0.2 to about 10 mg/kg lung dose, wherein a total daily dose of inhaled cytidine analogue compound or derivative thereof does not exceed 1000 mg/kg, and wherein the therapeutically effective dose treats cancer in the subject. In one embodiment, the aerosolization of the dry powder cytidine analogue compound (i) provides: a mass median aerodynamic diameter (MMAD) of particle size of the dry powder emitted with the aerosolizer of about 0.5 um to about 5 um; (ii) provides a Geometric Standard Deviation (GSD) of emitted particle size distribution of the dry powder of about 1.0 um to about 3.4 um; (iii) provides a fine particle fraction (FPF=% of aerosol particles less than or equal to 5 microns) of particle emitted from the dry powder of at least about 30%; and (iv) provides an emitted fraction from a device and capsule of at least about 50% or 60% or 70% or 80% or 90%. In another embodiment of the method of treating, a plasma C max and/or AUC of the cytidine analogue compound that is obtained after a single inhaled administration of the dry powder aerosolized to the subject is greater than the plasma C max and/or AUC of the cytidine analogue compound thereof obtained after a singled inhaled aqueous administration of the cytidine analogue compound nebulized to the subject at a dose that is the same as the dose administered with the inhaled dry powder cytidine analogue compound. In yet another method of treating, a brain C max and/or AUC of the cytidine analogue compound that is obtained after a single inhaled administration of the dry powder aerosolized to the subject is greater than the brain C max and/or AUC of the cytidine analogue compound obtained after a singled inhaled aqueous administration of an the cytidine analogue compound nebulized to the subject at a dose that is the same as the dose administered with the inhaled dry powder cytidine analogue compound. In a further embodiment of the method of treating, a liver C max and/or AUC of the cytidine analogue compound that is obtained after a single inhaled administration of the dry powder aerosolized to the subject is greater than the liver C max and/or AUC of the cytidine analogue compound obtained after a singled inhaled administration of an aqueous cytidine analogue compound nebulized to the subject at a dose that is the same as the dose administered with the inhaled dry powder cytidine analogue compound. In a further embodiment of the method of treating, a lung C max and/or AUC of the cytidine analogue compound that is obtained after a single inhaled administration of the dry powder aerosolized to the subject is greater than the lung C max and/or AUC of cytidine analogue compound obtained after a single systemic administration of an aqueous cytidine analogue compound to the subject at a dose that is three fold higher than the dose administered with inhaled dry powder cytidine analogue compound. The composition pulmonary delivered to the subject may include an excipient.

Another embodiment of the present invention provides a pharmaceutical kit comprising an inhalable powder composition comprising the inhalable powder composition comprising a cytidine analogue including salts, solvates, hydrates, and esters thereof and a pharmaceutically acceptable excipient; and a dry powder inhaler.

Another embodiment of the present invention provides a container comprising an inhalable powder composition as described herein.

One aspect of the present invention relates to the development and method of making and using a stable dry powder formulation of a cytidine derivative or analogue (such as 5AZA), a pyrimidine ring analogue of cytidine for use as an active agent in the treatment of cancer for example non-small cell lung cancer (NSCLC) via inhalation of inhalable dry particles comprising the active agent. In reference to the inhalable particles, "stable" or "stability" refers to the lack of chemical degradation of the active agent for example a cytidine analogue such as 5AZA to N-formylribosylguanylurea and/or ribosyl-guanylurea prior to administration and to the physical stability of the active agent and/or formulation in its ability to remain viable for inhalation delivery (20). In one embodiment, dry powder refers to a formulation of a cytidine analogue composition for example as a cytidine analogue active agent and a pharmaceutically acceptable excipient that is viable for delivery to the subject via inhalation of the dry powder.

One embodiment of the present invention provides for a cytidine analogue dry powder composition for inhalation by a subject in need thereof.

Another embodiment of the present invention provides for targeted delivery of a cytidine analogue such as 5AZA to the lung tissue that achieves tissue concentrations of between about [25-500 ug/ml] to achieve clinical effects while minimizing systemic toxicities.

Another aspect on one embodiment of the present invention provides for inhaled delivery of a cytidine analogue such as 5AZA compound/composition by direct deposition through the lung bronchial airways and alveoli and the pulmonary circulation.

Another embodiment of the present invention provides for a cytidine analogue such as 5AZA compound for delivery to bulky tumors with concentrations in bulky tumors to be comparable or exceed infusion chemotherapeutics of the aqueous cytidine analogue such as a 5AZA compound/composition concentrations in bulky tumors.

Another embodiment of the present invention provides for a method to treat extrapulmonary metastatic cancer in a subject in need of treatment wherein the treatment includes administering an effective amount of a dry powder cytidine analogue such as a 5AZA dry powder compound that is inhaled by a subject in need of the treatment. It is estimated that extrapulmonary metastatic cancer is present in ~40% of patients at diagnosis of lung cancer wherein conventional therapy in the form of chemotherapeutic drugs provides minimal effectiveness to the extrapulmonary metastatic disease based on 5-year survival of less than 10%.

Another embodiment of the present invention provides for an inhalable dry powder cytidine analogue such as a 5AZA compound wherein the absorption of the aerosolized dry powder cytidine analogue into the pulmonary vasculature avoids hepatic first pass, circumventing individual differences in cytidine deaminase activity to thereby permit the delivery of drug systemically to treat metastases that include LC.

One aspect of the present invention provides for the addition of DMSO as a diluent for stabilizing the cytidine analogue compound.

Another embodiment of the present invention provides for a cytidine analogue compound with a DMSO diluent that exhibits improved stability and/or less degradation during the spray drying process, and/or during vacuum desiccation to enable long-term storage.

Another embodiment of the present invention provides for an active dry powder formulation of a cytidine analogue with carrier excipients.

One aspect of a cytidine analogue powder formulation is that the formulation can be efficiently delivered into the lungs of humans and non-clinical species.

Another aspect of one embodiment of the present invention provides for an increase in lung tissue exposure of a cytidine analogue such as a 5AZA by at least 3, 5, 10 or 20-fold when compared to a systemic dose delivered via subcutaneous, IV or other non-inhalation routes when provided at the same concentration or lower concentration of the cytidine analogue such as a 5AZA. Inhalation delivery of the dry powder formulation of the cytidine analogue may increase lung tissue exposure to the cytidine analogue such as a 5AZA by about 47-fold when compared to a 3-times greater systemic dose of the cytidine analogue such as a 5AZA.

One aspect of one embodiment of the present invention provides for a pharmaceutical composition comprising a cytidine analogue dry powder formulation that should be effective in treating NSCLC in the lungs of patients.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings:

FIG. 4 illustrates a method of preparing a dry powder 5AZA formulation for inhalation according to one embodiment of the present invention.

DETAILED DESCRIPTION OF THE INVENTION

Figure 1A:
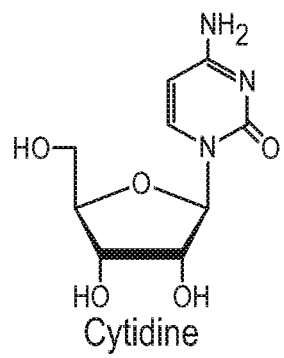
FIG. 1A-E illustrates cytidine and derivatives/analogues of the nucleoside cytidine.
Figure 1B:
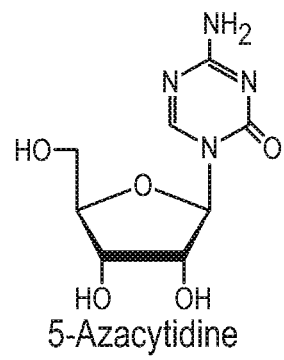
Figure 1C:
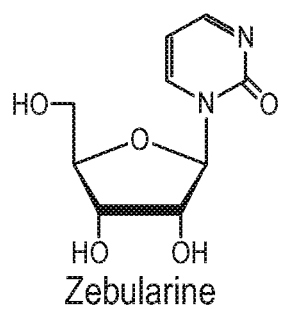
Figure 1D:
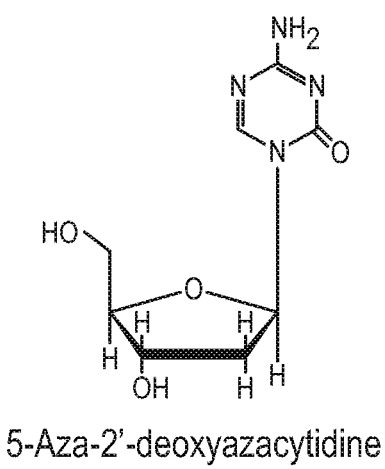
Figure 1E:
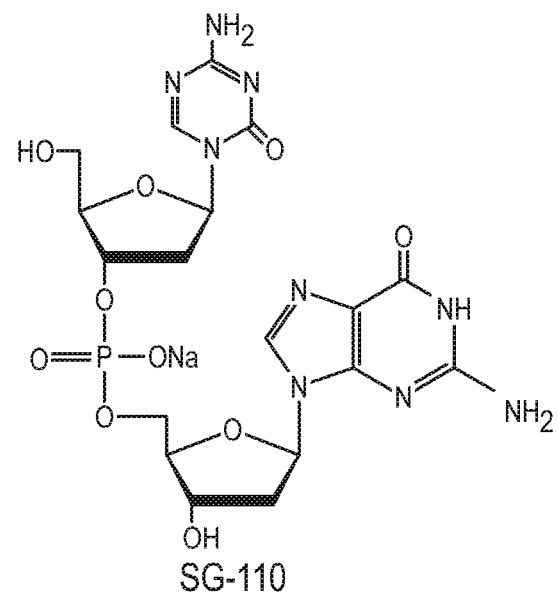
Figure 2A:
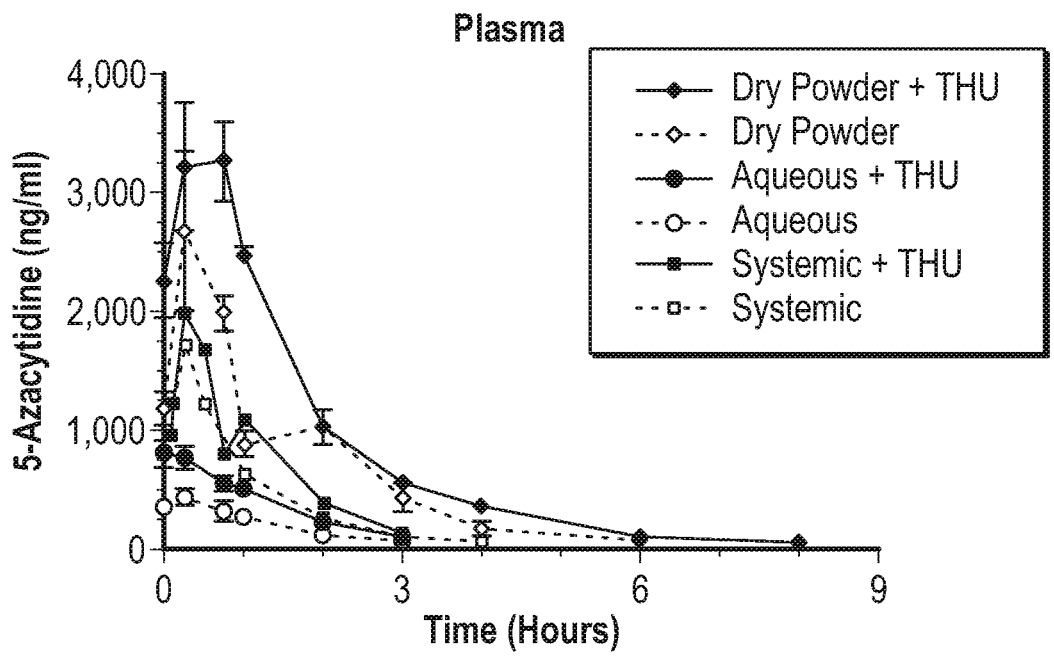
FIG. 2A-D illustrates pharmacokinetic profile of inhaled 5AZA dry powder compound according to one embodiment of the present invention as compared to inhaled aqueous 5AZA compound and systemic delivery of 5AZA compound delivered intraperitoneally in the Sprague Dawley rat. Rats were exposed to a single dose of 5AZA compound powder as i) inhaled dry powder [0.6 mg/kg lung dose], ii) inhaled aqueous [0.6 mg/kg lung dose], or iii) systemic (2 mg/kg, i.p.) and sacrificed over multiple time points to collect blood, liver, lung, and brain. A second set of animals received tetrahydrouridine ([THU], 80 mg/kg, oral dose) 1 hour prior to exposure to 5AZA.
Figure 2B:
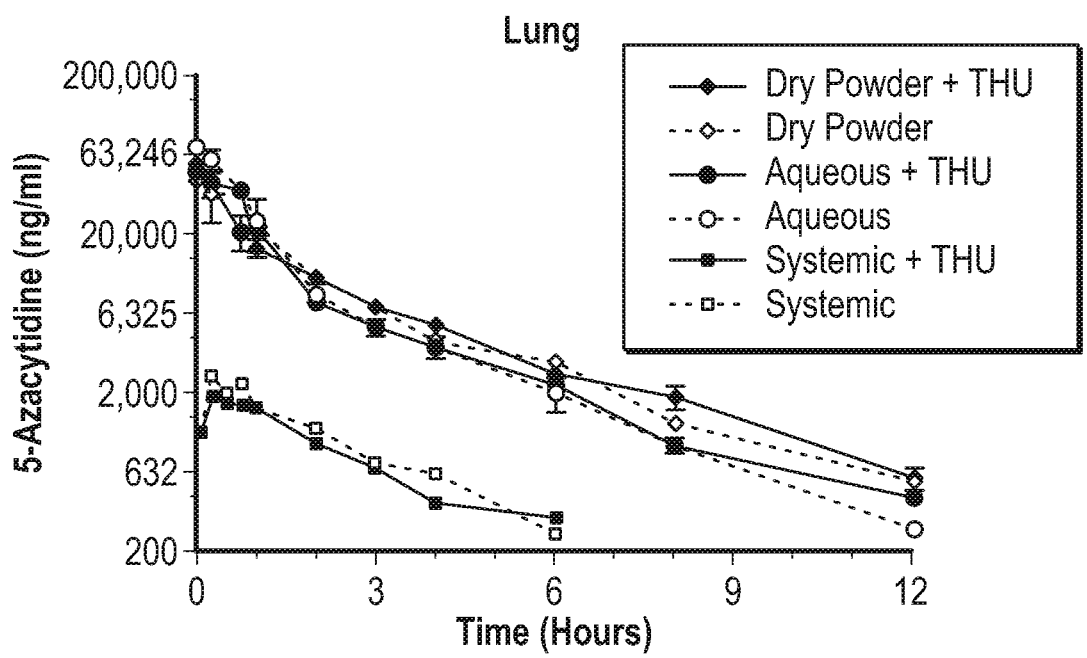
Figure 2C:
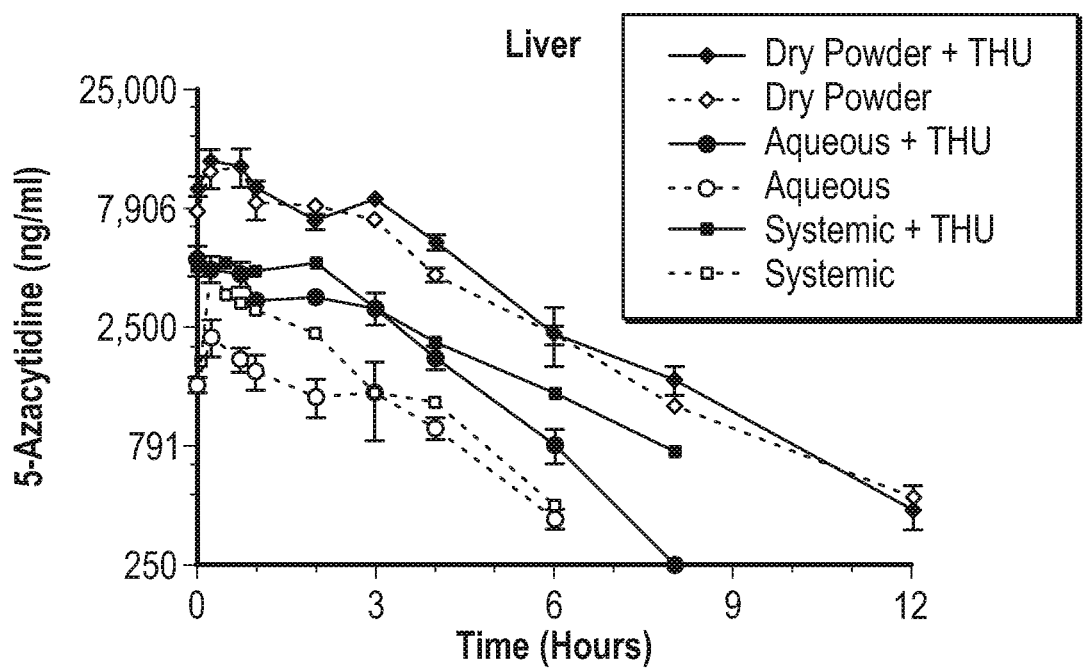
Figure 2D:
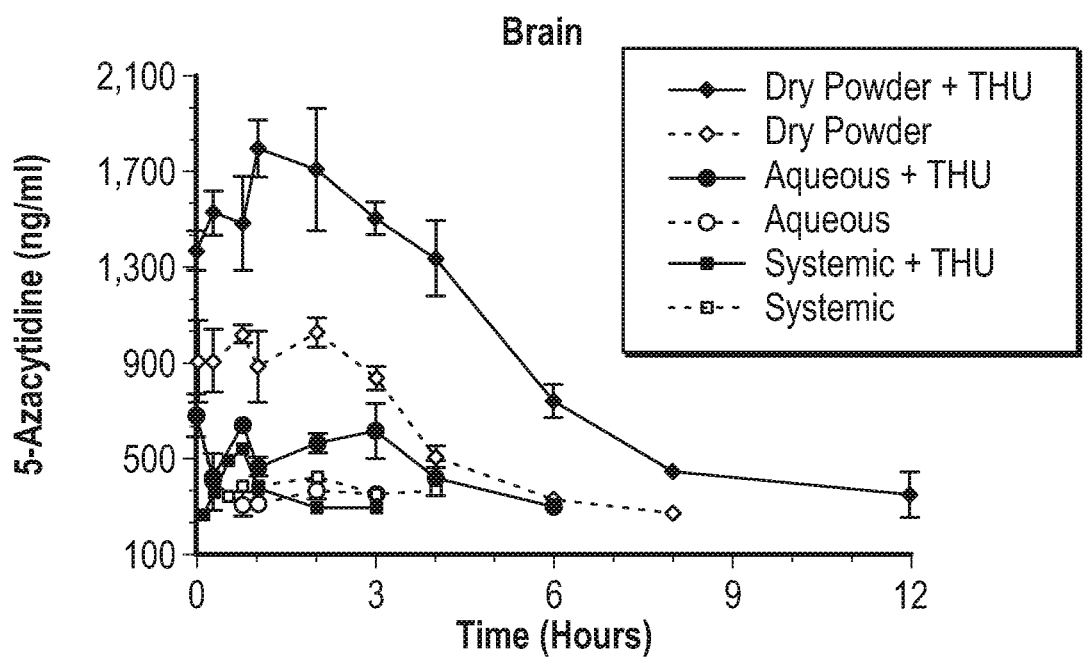

As used herein "a", "an" or "the" refers to one or more unless otherwise indicated.

When a compound provided herein contains one or more acidic or basic moieties, the compound may exist as a salt.

When a compound provided herein contains an acidic or basic moiety, it may also be provided as a pharmaceutically acceptable salt (21). As used herein, and unless otherwise specified, the term "pharmaceutically acceptable salts" refers to salts prepared from pharmaceutically acceptable non-toxic acids, including inorganic acids and organic acids, or pharmaceutically acceptable non-toxic bases, including inorganic bases and organic bases.

In one embodiment, provided herein is a pharmaceutically acceptable salt of a cytidine analogue such as a 5AZA, including, but not limited to hydrochloric acid salt, sulfuric acid salt, hydrobromic acid salt, and methanesulfonic acid salt.

In one embodiment, provided herein is a salt of a cytidine analogue such as a 5AZA that is substantially free of one or more impurities, such as for example, a metal-based impurity. In one embodiment, provided herein is a pharmaceutically acceptable salt of a cytidine analogue such as a 5AZA that is substantially free of one or more impurities, such as for example, a metal-based impurity.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate (e.g., mono-hydrate, dihydrate, trihydrate, tetrahydrate, and the like).

As used herein, and unless otherwise indicated, the term "polymorph" refers to a solid crystalline form of a compound provided herein or a salt or complex thereof. Different polymorphs of the same compound can exhibit different physical, chemical, biological, and/or spectroscopic properties, among others.

As used herein, and unless otherwise specified, the term "stereoisomer" encompasses all enantiomerically/stereomerically pure and enantiomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

In certain embodiments, as used herein, and unless otherwise specified, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

As used herein, and unless otherwise specified, the term "racemic" or "racemate" refers to about 50% of one enantiomer and about 50% of the corresponding enantiomer relative to all chiral centers in the molecule.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

Unless otherwise specified, the compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

It should be noted that where structural isomers are inter-convertible, the compound provided herein may exist as a single tautomer or a mixture of tautomers. This can take the form of proton tautomerism in the compound that contains, for example, an amino, keto, or oxime group; or so-called valence tautomerism in the compound that contain an aromatic moiety. It follows that a single compound may exhibit more than one type of isomerism.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, and unless otherwise specified, a composition that is "substantially free" of a compound means that the composition contains less than about 20% by weight, less than about 10% by weight, less than about 5% by weight, less than about 3% by weight, less than about 1% by weight, less than about 0.1% by weight, less than about 0.01% by weight, less than about 0.001% by weight, or less than about 0.0001% by weight of the compound.

As used herein, and unless otherwise specified, a composition that is "substantially pure" means that the composition has a purity level of greater than about 80% by weight, greater than about 90% by weight, greater than about 95% by weight, greater than about 97% by weight, greater than about 99% by weight, greater than about 99.5% by weight, greater than about 99.9% by weight, greater than about 99.95% by weight, greater than about 99.99% by weight, greater than about 99.995% by weight, greater than about 99.999% by weight, greater than about 99.9995% by weight, or greater than about 99.9999% by weight.

As used herein, and unless otherwise specified, the term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio (22-26).

As used herein, and unless otherwise specified, the terms "active ingredient," "active substance," or "active pharmaceutical ingredient" refers to a compound or a substance, which is administered, alone or in combination with other pharmaceutically active compound(s), and/or one or more pharmaceutically acceptable excipients, to a subject for treating, preventing, and/or ameliorating one or more symptoms of a condition, disorder, or disease. As used herein, "active ingredient," "active substance," and "active pharmaceutical ingredient" may be a pharmaceutically acceptable salt, solvate, hydrate, ester, polymorph, or optically active isomer of a compound described herein.

Cancers are classified in two ways: by the type of tissue in which the cancer originates (histological type) and by primary site (the location in the body where the cancer first developed). From a histological standpoint there are hundreds of different cancers, which are grouped into six major categories: Carcinoma, Sarcoma, Myeloma, Leukemia, Lymphoma, Mixed Types, Central Nervous System and Mesothelioma as identified from the world wide web cancer research society website crs-src.ca last visited on May 5, 2016.

The term "cancer" is used throughout the specification to refer to a cell(s) possessing one or more of the following abnormal growth characteristics: uncontrolled proliferation, immortality, metastatic potential, rapid growth and proliferation rate, perturbed oncogenic signaling, and certain morphological characteristic features and may originate from: epithelial cell tissue (carcinomas), blood cells, bone marrow, and immune cells (leukemias, lymphomas, myelomas), connective tissue, bone, cartilage, fat, muscle, blood vessels (sarcomas), central nervous system tissue, glial or supportive cells (gliomas, blastomas CNS lymphoma), mesothelium lining (mesothelioma of lung, heart, abdominal cavity), melanoma (mesodermal origin). As used herein, the term cancer is used to describe all cancerous disease states applicable to diagnosis and treatment according to the present invention and embraces or encompasses the pathological process associated with virtually all cancers types, including carcinomas, sarcoma, myeloma, leukemia, lymphoma, mixed types. In a preferred embodiment, the cancer is a solid tumor.

The term "lung cancer" includes cancer found in the lung regardless as to whether the cancer originated in lung or the cancer originated in another tissue and metastasized to the lung, for example breast cancer that metastasized to the lung.

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease or prior diagnosis of the disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human.

Unless otherwise specified, the compound provided herein may be provided as a prodrug, which is a functional derivative of the compound, for example, SG-110 is readily convertible into the parent compound 5-aza-2'-deoxycytidine in vivo (9). Prodrugs are often useful because, in some situations, they may be easier to administer than the parent compound. They may, for instance, be bioavailable by inhaled administration whereas the parent compound is not. The prodrug may also have enhanced solubility in pharmaceutical compositions over the parent compound. A prodrug may be converted into the parent drug by various mechanisms, including enzymatic processes and metabolic hydrolysis.

As used herein, and unless otherwise indicated, the term "process" refers to the methods disclosed herein which are useful for preparing a compound provided herein. Modifications to the methods disclosed herein (e.g., starting materials, reagents, protecting groups, solvents, temperatures, reaction times, purification) that are well known to those of ordinary skill in the art are also encompassed by the present disclosure.

An object of the present invention is to provide a pharmaceutical composition suitable for long-term pulmonary administration to a patient in need thereof.

Another object of this invention is to provide a pharmaceutical-containing dispersible dry powdered composition that is administered by inhalation in a manner that contains a liquid propellant such as a CFC, HFC or carbon dioxide or in another embodiment the dry powdered composition is administered by inhalation in a manner that is free of a liquid propellant such as a CFC, HFC or carbon dioxide.

Another object of this invention is to provide a pharmaceutical-containing dispersible dry powdered composition that can be easily manufactured by a method that maintains a high percentage of pharmaceutical activity.

Another object of this invention is to provide a manufacture method for the production of pharmaceutical composition of sufficient purity.

Still another object of this invention is to provide a pharmaceutical-containing dispersible dry powdered composition that exhibits a high level of stability.

The term "disperse ability" or "dispersible" means a dry powder having a moisture content of less than about 15% by weight (% w) water, usually below about 5% w and preferably less than about 3% w; a volumetric particle size of about 1.0-10.0 µm and an aerodynamic particle size of 1.0-8.0 mass median aerodynamic diameter (MMAD), usually 1.0-5.0 µm MMAD, and preferably 1.0-4.0 µm MMAD; a delivered dose of about >30%, usually >40%, preferably >50%, and most preferred >60%; and an aerosol particle size distribution of about 1.0-5.0 µm mass median aerodynamic diameter (MMAD), usually 1.5-4.5 µm MMAD, and preferably 1.5-4.0 µm MMAD.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average MMAD of the powder is less than about 10 microns (μm) in diameter with a relatively uniform spheroidal shape distribution. More preferably the diameter is less than about 7.5 μm and most preferably less than about 5.0 μm. Usually the particle size distribution is between about 0.1 μm and about 5 μm in diameter, particularly about 0.3 μm to about 5 μm.

The term "dry" means that the composition has moisture content such that the particles are readily dispersible in an inhalation device to form an aerosol. This moisture content is generally below about 10% by weight (% w) water, usually below about 5% w and preferably less than about 3% w.

The term "inhalable" or "inhalation" refers to particles that are suitable for pulmonary administration. Such particles have a mean aerodynamic particle size of less than 10 μm, more preferably less than 5 μm and most preferably less than 3.5 μm.

The term amino acid such as leucine, trileucine, isoleucine is intended to encompass salt forms or counterion formulations of the amino acid as well as isolated stereoisomers (e.g. D-Leucine or L-leucine) and mixtures of stereoisomers. Derivatives and intermediates of the amino acid such as leucine, trileucine, isoleucine are also encompassed. The amino acids may be selected from aspartic acid, glutamic acid, leucine, isoleucine, lysine, valine, methionine, phenylalanine, glycine, arginine, aspartic acid, glutamic acid, cysteine, alanine, serine, N-acetyl-cysteine, phenylalanine, lysine, or pharmaceutically acceptable derivatives, salts, solvates, hydrates, and polymorphs thereof.

Referring now to FIG. 1A-E, cytidine and derivatives/analogues thereof are illustrated. The cytidine analogues include the salts, solvates, hydrates, and esters thereof (27). One or more of the cytidine analogues are thought to act as inhibitors of DNA methyltransferase and of uridine kinase. The effects of cytidine analogues occur through its incorporation into DNA as a nucleotide and result in the death of rapidly dividing cells, including cancer cells that are no longer responsive to normal cell growth control mechanisms. cytidine analogues also incorporate into RNA. The cytotoxic effects of cytidine analogues may result from multiple mechanisms, including inhibition of DNA, RNA and protein synthesis, incorporation into RNA and DNA, and activation of DNA damage pathways. The cytidine analogue 5-Azacitidine (5AZA) having chemical name 4-amino-1-β-D-ribofuranosyl-1,3,5-triazin-2(1H)-one is an inhibitor of DNA methyltransferase and of uridine kinase. The effects of 5AZA through its incorporation into DNA result in the death of rapidly dividing cells, including cancer cells that are no longer responsive to normal cell growth control mechanisms. 5AZA also incorporates into RNA. The cytotoxic effects of 5AZA may result from multiple mechanisms, including inhibition of DNA, RNA and protein synthesis, incorporation into RNA and DNA, and activation of DNA damage pathways. Current 5AZA therapy combines a 5AZA powder with a mannitol powder that is dissolved in sterile water for subcutaneous systemic delivery to treat certain types of bone marrow cancers and blood cell disorders. While 5AZA is an effective DNA demethylating agent in vitro leading to re-expression of genes that contribute to its effects, its activity and half-life is limited in vivo via subcutaneous delivery by first pass deactivation in the liver by cytidine deamination, a barrier that limits its activity against LC. The development of dry powder formulations delivered as aqueous or dry powder aerosols directly to the lungs provide a unique opportunity to greatly improve the pharmacokinetic profile and to substantially increase the concentration of 5AZA at the tumor site, thereby facilitating enhanced cytosine demethylation, gene re-expression and clinical response in the form of tumor regression.

A validated orthotopic LC model that recapitulates LC in humans with respect to local drug delivery PKs and tumor heterogeneity is useful to assess the efficacy of aerosol delivery of the different formulations of 5AZA and the synergistic potential of agents targeting chromatin remodeling for affecting tumor burden and gene re-expression.

An orthotopic LC model was developed in which xenografts of human LC-derived cell lines are efficiently engrafted throughout the lungs of the Rowett nude rat (28). One study in this rat model evaluated combination therapy comprising systemic delivery via intraperitoneal injection of 5AZA reconstituted in sterile water and the histone deacetylase HDACi entinostat (MS275) delivered to the rats at doses and schedule similar to the Phase II clinical trial with 5AZA and MS275 administered to patients with refractory, advanced non-small cell lung cancer. 5AZA reduced tumor burden by 31%, while MS275 was synergistic with 5AZA to suppress tumor growth by 60%. 5AZA induced reprogramming of the epigenome as detected by gene demethylation and re-expression (29). Further, a highly respirable aqueous aerosol formulation of 5AZA (5AZA reconstituted in sterile water) was used for inhaled nebulizer delivery. An inhaled nebulized dose of about 0.6 mg/kg 5AZA was delivered to the rats and the dose was compared to the systemic intraperitoneal dose of 2 mg/kg 5AZA reconstituted in sterile water. The comparison showed that inhaled delivery of aqueous 5AZA yielded an improved PK profile in the lung, equivalent reduction in tumor burden, and enhanced commonality for demethylation of 300 genes in tumors sampled throughout lung lobes at one-third of the effective systemic 5AZA dose (30). Qiu et al. replicated our findings in an orthotopic mouse model and this group has initiated a Phase I dose escalation safety and biomarker study in humans that is ongoing with nebulized 5AZA (31, 32).

Nebulizing drugs for cancer therapy are constrained by extended time for delivery, required administration in the clinic, and the chemical stability of the 5AZA over the delivery period. Thus, to obviate these barriers, a novel spray dried formulation of 5AZA described below was developed that proved to have superior physical and chemical stability, PK properties, and efficacy for treatment of lung cancer as compared to inhaled aqueous 5AZA.

One aspect of the present invention provides for generating a dry powder formulation of 5AZA that is advantageous through enabling a chemically and physically stable formulation with properties suitable for clinical and non-clinical delivery.

One component of a dry powder formulation of cytidine analogue such as 5AZA for example is a diluent that stabilizes the drug, maintains stability during the manufacturing process, and retains stability during storage of the product prior to use. Several diluents were evaluated that included ammonium acetate buffer, unbuffered water, 1:1 ethanol:water, and DMSO. DMSO provided the stability and solubility that was desired. DMSO has not been used in any marketed/approved inhalation product and was not obvious to try. While toxicity of DMSO has not been evaluated via inhalation, intravenous dosing in rats at 200 mg/kg (2,000 times greater than our inhaled 5AZA dose) for a month showed no toxicity (33).

In one embodiment, 5AZA was mixed with DMSO (10%) to prevent degradation of 5AZA during the spray drying process. Excipients such as a carbohydrate for example such as a sugar (for example trehalose) and/or an amino acid (for example leucine) are added to drive the spray drying process. The formation of a dry powder that is flowable and respirable included the steps of solubilizing for example in water or saline an excipient comprising trehalose and leucine and in-line mixing the excipient with the DMSO-5AZA just prior to atomization. These excipients are believed to interact based on their solubility in the droplet. As the droplet evaporates each excipient reaches its solubility maximum. When the solubility is above maximum saturated solubility the excipient crystallizes. Trehalose serves as a high glass transition temperature bulking agent to help with particle formulation and dose dilution. Leucine is the first to crystallize and it drives the spherical shape of the particle and the porous nature of the particle. Leucine is one of the amino acids used in facilitating the aerosol performance and stability of spray-dried powders for inhalation. Others include, but are not limited to, trileucine and isoleucine (34). Trehalose serves as fine particles in dry powder formulations to improve the inhalation efficiency of drugs that include cytidine analogues such as 5AZA. Other suitable fine powders derive from a large list of sugars, hexahydric alcohols, and sugar alcohols that include, but are not limited to lactose, mannitol, sorbitol, raffinose, inositol and erythritol (35).

In one embodiment of the present invention a cytidine analogue composition comprises trehalose/leucine/5AZA with residual DMSO in the ratio of about 70/20/10 w/w with about 11% DMSO, however other ratios are possible. Scanning electron microscopy revealed that the formulation was composed of primary particles with no signs of fusion or agglomeration. HPLC analysis revealed chemical purity of about 98% or greater with no degradation detected after spray drying or following vacuum desiccation (approach used for stable storage). In one embodiment of the invention, the cytidine analogue is present in an amount less than or equal to about 99% by weight of the dry weight of the powder composition, for example less than or equal to about 90%, such as less than or equal to about 80% or 70% or less than or equal to about 60% or less than or equal to about 50%, or less than or equal to about 40%, or less than or equal to about 30%, or less than or equal to about 20% or less than or equal to about 10%. The cytidine analogue may be present in an amount greater than or equal to about 0.5%, about 1%, about 2%, about 3% or about 4% by weight of the dry weight of the powder composition. For example, in one embodiment the cytidine analogue is present in an amount of from about 0.5% to about 5%, or about 5% to about 10% or about 10% to about 20% by weight of the dry weight of the composition. For example, in one embodiment the cytidine analogue is present in an amount of from about 1% to about 20% or about 5% to about 15% of the dry weight of the composition.

In one embodiment of the invention, the pharmaceutically accepted excipient is present in an amount less than or equal to about 99% by weight of the dry weight of the powder composition, for example less than or equal to about 90%, such as less than or equal to about 80% or 70% or less than or equal to about 60% or less than or equal to about 50%, or less than or equal to about 40%, or less than or equal to about 30%, or less than or equal to about 20% or less than or equal to about 10%. Alternatively, the pharmaceutical acceptable excipient may be absent (0%) or present in an amount greater than or equal to about 0.5%, about 1%, about 2%, about 3% or about 4% by weight of the dry weight of the powder composition. For example, in one embodiment the pharmaceutical acceptable excipient is present in an amount of from about 0.5% to about 5%, or about 5% to about 10% or about 10% to about 20% by weight of the dry weight of the composition. For example, in one embodiment the pharmaceutical acceptable excipient is present in an amount of from about 60% to about 70% or about 65% to about 75% of the dry weight of the composition. Alternatively, the pharmaceutical acceptable excipient is present in an amount of from about 0.5% to about 5%, or about 5% to about 10% or about 10% to about 20% by weight of the dry weight of the composition. For example, in one embodiment the pharmaceutical acceptable excipient is present in an amount of from about 50% to about 80% or about 65% to about 75% of the dry weight of the composition.

In one embodiment of the invention, the leucine and/or trileucine, and/or isoleucine is present in an amount less than or equal to about 99% by weight of the dry weight of the powder composition, for example less than or equal to about 90%, such as less than or equal to about 80% or 70% or less than or equal to about 60% or less than or equal to about 50%, or less than or equal to about 40%, or less than or equal to about 30%, or less than or equal to about 20% or less than or equal to about 10%. Alternatively, the leucine and/or trileucine, and/or isoleucine may be absent (0%) or present in an amount greater than or equal to about 0.5%, about 1%, about 2%, about 3% or about 4% by weight of the dry weight of the powder composition. For example, in one embodiment the leucine and/or trileucine, and/or isoleucine is present in an amount of from about 0.5% to about 5%, or about 5% to about 10% or about 10% to about 20% by weight of the dry weight of the composition. For example, in one embodiment the leucine and/or trileucine, and/or isoleucine is present in an amount of from about 10% to about 30% or about 15% to about 25% of the dry weight of the composition.

In one embodiment of the invention, the trehalose is present in an amount less than or equal to about 99% by weight of the dry weight of the powder composition, for example less than or equal to about 90%, such as less than or equal to about 80% or 70% or less than or equal to about 60% or less than or equal to about 50%, or less than or equal to about 40%, or less than or equal to about 30%, or less than or equal to about 20% or less than or equal to about 10%. Alternatively, the trehalose may be absent (0%) or present in an amount greater than or equal to about 0.5%, about 1%, about 2%, about 3% or about 4% by weight of the dry weight of the powder composition. For example, in one embodiment the trehalose is present in an amount of from about 0.5% to about 5%, or about 5% to about 10% or about 10% to about 20% by weight of the dry weight of the composition. For example, in one embodiment the trehalose is present in an amount of from about 55% to about 90% or about 65% to about 75% of the dry weight of the composition.

In another embodiment of the invention, the trehalose analogue is present in an amount less than or equal to about 90% or 80% or 70% or 60% by weight of the dry weight of the powder composition, the leucine and/or trileucine, and/or isoleucine is present in an amount of about 5% or from about 10% to about 25% by weight of the dry weight of the powder composition and the cytidine analogue is present in an amount of about 1-25% or from about 5% to about 15% by weight of the dry weight of the powder composition.

In another embodiment, the residual DMSO is about 0-5%, 5-10%, 10-20% or less than 30%.

The particle size distribution of the dry powder formulation was characterized from a capsule-based inhaler (Plastiape RS01) with a Next Generation Impactor (NGI, MSP Corp) to determine mass mean aerodynamic diameter (MMAD), geometric standard deviation (GSD), emitted fraction from device and capsule (EF), and fine particle fraction (FPF) for the powder (Table 1). The Plastiape device was selected because it is translatable to clinical delivery when the program advances to clinical studies. Duplicate analysis was performed on all testing and the results were compared for reproducibility. The FDA requirement that all orally inhaled aerosols must have an MMAD of 1-5 μm that reduces oral deposition and increases pulmonary deposition. In one embodiment of the present invention, an inhalable 5AZA dry powder formulation as disclosed herein was characterized to have an MMAD of about 3.5 μm±0.3.

TABLE 1

Physicochemical properties of the spray-dried powder formulation 5-azacytidine

| Formulation (w/w %) | 70/20/10 (trehalose/L-leucine/5AZA) |
|---|---|
| MMAD (μm) | 3.5 ± 0.3 |
| GSD (Geometric Standard deviation) | 1.6 ± 0.2 |
| EF % (Capsule + Device) (Emitted Fraction) | 90.6 |
| FPF % (<5 μm) (Fine particle Fraction) | 48 |

A pharmacokinetics study was conducted to compare the properties of a systemic (2 mg/kg, intraperitoneal injection [i.p.]) dose that is equivalent to the human injectable dose of 75 mg/m$^2$, inhaled aqueous (0.6 mg/kg lung dose), and inhaled dry powder (0.3, 0.6, and 0.9 mg/kg lung dose) formulation of 5AZA in blood, lung, (Table 2) and liver, and brain (Table 3) in the Sprague Dawley rat following exposure to a single dose of 5AZA. The 5AZA aerosol was delivered into the lungs of rats using a nose only inhalation delivery system in which a 5AZA dry powder formulation and a 5AZA aqueous formulation aerosol is generated with a rotating brush generator or Pari nebulizer, respectively. The system monitors the total aerosol concentration, 5AZA aerosol concentration and particle size distribution. In addition, the effect of a cytidine deaminase (CDA) inhibitor tetrahydrouridine (THU, [80 mg/kg]) administered orally one hour prior to 5AZA dosing on pharmacokinetics was determined. Following 5AZA administration, 3 animals per treatment-group per time-point were serially sacrificed at 10 time-points over 12 hours. At each time-point, systemic blood was collected into $K_3$EDTA tubes for separation into plasma and lung, liver, and brain tissue was snap frozen in liquid nitrogen. Plasma and lung tissue samples were assayed via a liquid chromatography mass spectrometry assay and the average concentration versus time profile modeled with non-compartmental analysis. Pharmacokinetic profile of inhaled dry powder 5AZA formulation was compared to inhaled aqueous 5AZA formulation and systemic 5AZA formulation (i.p. injection) in the Sprague Dawley rat (FIG. 2). This comparison used rats exposed to a single dose of (inhaled dry powder 5AZA [0.6 mg/kg lung dose], inhaled aqueous 5AZA [0.6 mg/kg lung dose], or systemic 5AZA (2 mg/kg, i.p.) with and without administration of THU (80 mg/kg oral dose).

The addition of THU increased the area under the curve (AUC) in plasma for all but the highest dose of dry powder (may have saturated the THU dose) and the maximum plasma concentration (C max [Table 2]). Most striking and independent of THU, was a ~10-fold increase in AUC for the dry powder and a 1.5 and 5-fold increase in C max when comparing the inhaled dry powder 5AZA (0.6 mg/kg) to systemic 5AZA (2 mg/kg) and inhaled aqueous 5AZA (0.6 mg/kg) 5AZA, respectively (Table 2; FIG. 2).

Inhalation delivery of the 5AZA dry powder formulation yields a plasma AUC and C max that greatly exceed values seen for inhaled delivery of the aqueous 5AZA formulation or systemic delivery of the 5AZA formulation. Thus, inhalation delivery of the dry powder 5AZA (for example via a formulation as disclosed herein) is well suited to achieve improved systemic delivery to treat metastatic cancer in tissues outside of the lung, to reduce tumor burden and improve overall survival. This result was not obvious as one of ordinary skill in the art would not have identified inhaled 5AZA dry powder to exhibit an improved PK over the inhaled aqueous form of 5AZA.

The addition of THU did not influence lung PK (Table 2). Inhaled dry powder and aqueous 5AZA (0.6 mg/kg dose) showed comparable PK profiles that were superior to systemic delivery with respect to C max (~30-fold) and AUC (~47-fold). The PK analyses in the liver and brain show the superiority of the dry powder 5AZA compared to inhaled aqueous and systemic dosing with a 7-26-fold and 2.5-3.3-fold increase in AUC and C max, respectively (FIG. 2, Table 3). The addition of THU greatly improved the PK profile for the dry powder formulation in brain. These findings substantiate that inhaled delivery of dry powder 5AZA provides a systemic dose that is greatly superior to systemic or aqueous nebulized 5AZA that could be effective in treating metastatic disease.

TABLE 2

PK Parameters for Systemic and Inhaled Delivery of 5AZA in Blood and Lung

| Delivery Route | Dose (mg/kg) | THU | AUC (h × ng/ml) Plasma | AUC (h × ng/ml) Lung | Half-Life (min) Plasma | Half-Life (min) Lung | Cmax (ng/ml) Plasma | Cmax (ng/ml) Lung |
|---|---|---|---|---|---|---|---|---|
| Systemic | 2.0 | + | 1,195 | 2,925 | 36 | 124 | 1,990 | 1,882 |
| Systemic | 2.0 | − | 951 | 3,230 | 54 | 116 | 1,713 | 2,497 |
| Aerosol-Aq | 0.6 | + | 1,919 | 102,883 | 50 | 144 | 822 | 50,100 |
| Aerosol-Aq | 0.6 | − | 1,082 | 127,780 | 56 | 125 | 442 | 71,333 |
| Aerosol-DP | 0.3 | + | 10,565 | 142,031 | 63 | 153 | 1,453 | 24,900 |
| Aerosol-DP | 0.3 | − | 7,971 | 139,028 | 49 | 142 | 1,740 | 24,533 |
| Aerosol-DP | 0.6 | + | 11,209 | 142,713 | 76 | 172 | 3,267 | 56,217 |
| Aerosol-DP | 0.6 | − | 6,998 | 144,055 | 64 | 161 | 2,683 | 44,919 |
| Aerosol-DP | 0.9 | + | 8,841 | 168,611 | 76 | 144 | 4,127 | 115,167 |
| Aerosol-DP | 0.9 | − | 8,327 | 169,233 | 63 | 125 | 3,223 | 99,667 |

Abbreviations:
Aq, aqueous;
DP, dry powder
N = 3 animals/10 time points/group for determining PK parameters.

TABLE 3

PK Parameters for Systemic and Inhaled Delivery of 5AZA in Brain and Liver

| Delivery Route | Dose (mg/kg) | THU | AUC (h × ng/ml) Brain | AUC (h × ng/ml) Liver | Half-Life (min) Brain | Half-Life (min) Liver | Cmax (ng/ml) Brain | Cmax (ng/ml) Liver |
|---|---|---|---|---|---|---|---|---|
| Systemic | 2.0 | + | 706 | 11,870 | NC | 157 | 541 | 4,737 |
| Systemic | 2.0 | − | 421 | 5,922 | NC | 114 | 421 | 4,558 |
| Aerosol-Aq | 0.6 | + | 4,136 | 25,587 | NC | 97 | 677 | 4,768 |
| Aerosol-Aq | 0.6 | − | 1,008 | 11,757 | NC | 102 | 425 | 2,300 |
| Aerosol-DP | 0.3 | + | 7,370 | 67,695 | NC | 118 | 743 | 5,768 |
| Aerosol-DP | 0.3 | − | 5,021 | 46,372 | NC | 128 | 610 | 4,998 |
| Aerosol-DP | 0.6 | + | 18,987 | 87,438 | NC | 126 | 1,800 | 12,350 |
| Aerosol-DP | 0.6 | − | 8,401 | 80,262 | NC | 153 | 1,082 | 11,800 |
| Aerosol-DP | 0.9 | + | 9,578 | 48,866 | NC | 180 | 1,930 | 12,100 |
| Aerosol-DP | 0.9 | − | 8,488 | 39,398 | NC | 112 | 1,632 | 11,200 |

Abbreviations:
Aq, aqueous;
DP, dry powder
NC, not calculated due to not enough data points above lower limit of quantification.
N = 3 animals/10 time points/group for determining PK parameters.

An efficacy study comparing inhaled delivery of equivalent doses (0.6 mg/kg lung dose) of aqueous versus dry powder 5AZA was conducted in the orthotopic LC model. Two adenocarcinoma (AdC) tumor lines, Calu-6 and Calu-3, one bronchoalveolar (BAC) tumor line, H358, and one squamous cell carcinoma (SCC) line, RH2 that were derived from NSCLC patients were evaluated. The cell lines (15× $10^6$ cells/rat for Calu-6 and Calu-3, 7.5×$10^6$ cells/rat for H358 and RH2) were instilled via the trachea into the lungs of nude rats (60 rats per cell line). Six rats were kept cancer and treatment naïve to serve as normal control. Three weeks following engraftment of tumor lines (lungs contain numerous tumors 1-3 mm [20]), rats (n=20/group) were treated 4 times weekly for 4 weeks and then sacrificed to assess tumor burden. Five animals/group were held to evaluate survival post-therapy for Calu6 and Calu3. The lungs of all animals were immediately removed, weighed, and the tumor burden was determined by subtracting the weights of tumor bearing lungs from the average weights of tumor-free lungs. In addition, tumor naïve Sprague Dawley rats were exposed to the dry powder 5AZA under the same treatment protocol to evaluate local and systemic toxicity.

Figure 3A:
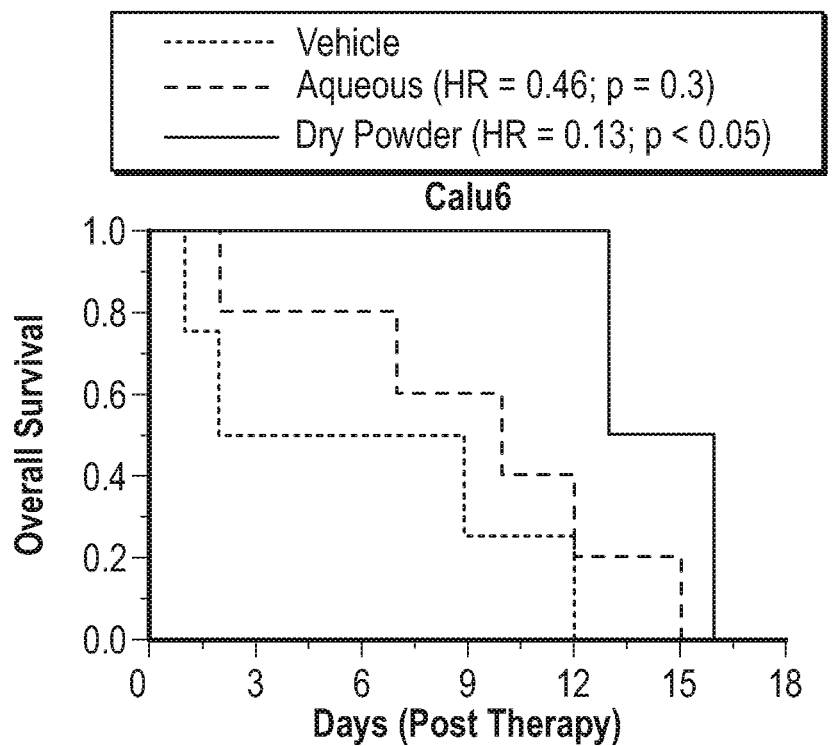
FIG. 3A-B illustrates survival of rats with Calu6 and Calu3 lung tumors treated with vehicle, 5AZA inhaled aqueous formulation and 5AZA inhaled dry powder formulation according to one embodiment of the present invention.
Figure 3B:
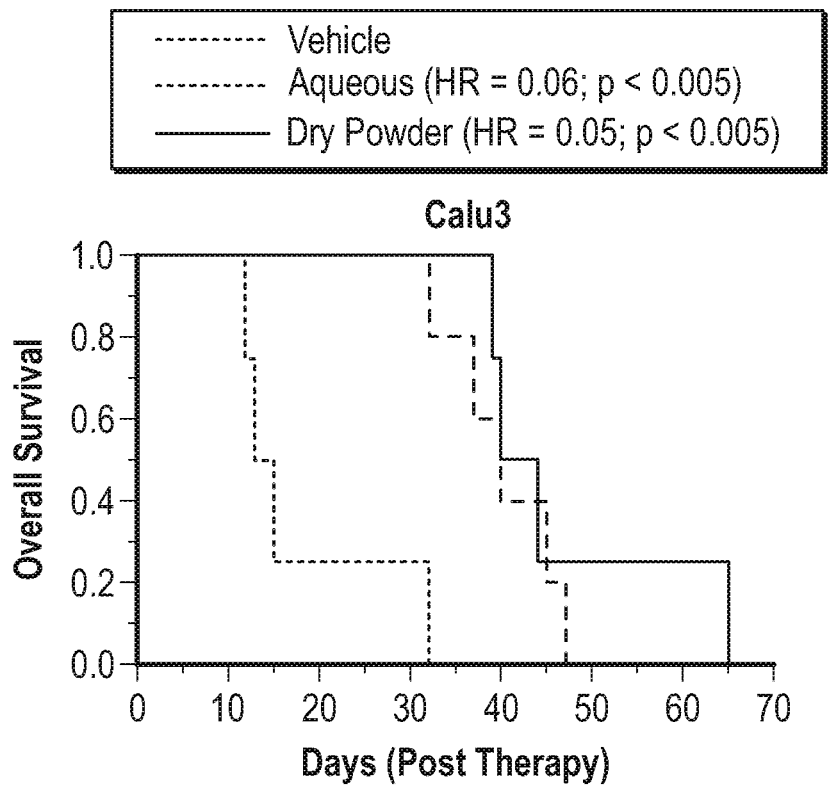

The inhaled dry powder 5AZA formulation was significantly better than the inhaled aqueous 5AZA formulation with a 70-80% reduction as compared to 50% reduction in tumor burden for Calu6 and Calu3 tumors, respectively (Table 4). The inhaled dry powder 5AZA formulation was also superior to the systemic i.p. 5AZA for reducing tumor burden for Calu6 tumors (80% versus 31% [29]). Both inhalation treatments were associated with improved survival of Calu3 tumors, while dry powder 5AZA formulation improved the survival of Calu6 tumors (FIG. 3). Treatment with either dry powder or aqueous 5AZA formulation was equally effective in largely curing the slower growing H358 bronchoalveloar tumors (Table 4). In contrast, the inhaled dry powder 5AZA formulation was far superior in affecting growth of the aggressive squamous cell carcinoma, RH2 as evident by a 74% reduction in tumor burden compared to a 33% reduction for the aqueous 5AZA formulation. There was also no histopathological evidence for local or systemic toxicity after 4 weeks of exposure to the inhaled 5AZA dry powder formulation. Together, these studies strongly support the use of this novel 5AZA dry powder formulation for the treatment of local and metastatic lung and other cancers.

TABLE 4

Effect of Inhaled 5AZA on Tumor Burden in an Orthotopic Rat Luna Cancer Model

| Cell Line | Tumor Type | Vehicle | Aqueous Tumor Burden (gms) | Dry Powder |
|---|---|---|---|---|
| Calu6 | AdC | 12.6 ± 4.3 | 6.2 ± 2.6[1] | 2.4 ± 1.2[1,2] |
| Calu3 | AdC | 6.5 ± 2.1 | 3.1 ± 0.9[1] | 1.9 ± 0.7[1,2] |
| H358 | BAC | 7.8 ± 3.6 | 0.4 ± 0.2[1] | 0.3 ± 0.4[1] |
| RH2 | SCC | 14.1 ± 3.0 | 9.5 ± 2.0[1] | 3.6 ± 2.1[1,2] |

Mean ± SD from 13-18 rats/group
[1]$p \leq 0.001$ comparing vehicle versus 5AZA aqueous or dry powder.
[2]$p \leq 0.003$ comparing 5AZA aqueous versus dry powder.

Inhalation delivery of a dry powder 5AZA formulation showed improved efficacy as compared to the aqueous 5AZA formulation for reducing tumor burden of adenocarcinoma and squamous cell carcinoma, and similar efficacy for bronchoalveolar carcinoma (see Table 4). These three tumor types comprise the broader lung cancer classification of non-small cell lung cancer (NSCLC). Thus, the 5AZA dry powder formulation for inhalation delivery is useful in treating NSCLC in the lungs of patients.

Inhalation delivery of a cytidine analogue, for example 5AZA dry powder formulation can improve overall survival of the subject for some tumors compared to the aqueous cytidine analogue, for example 5AZA formulation delivered via the same route.

The superior pharmacokinetic profile and efficacy for reducing tumor burden for the inhaled dry powder 5AZA compound as an example of a cytidine analogue support the use of inhaled dry powder cytidine analogue in epigenetic priming for improving progression free and overall survival when co-administered combined with immunotherapy or other therapies that may include chemotherapeutics and small molecule inhibitors.

Inhalation delivery of a dry powder compound cytidine analogue, for example 5AZA dry powder compound was not associated with toxicity to normal lung tissue or other systemic organs. Thus, inhalation delivery of the 5AZA dry powder compound can be used for adjuvant therapy given chronically to lung cancer patients following tumor resection to prevent recurrence and improve progression free and overall survival where chemotherapy has shown no effect (36).

One aspect of the inhaled dry powder 5AZA compound delivered at 0.6 mg/kg (low dose) to the lungs provides improved efficacy over the equivalent inhaled aqueous dose of 5AZA and the inhaled dry powder 5AZA dose can be increased further to reduce tumor growth in the lungs.

One aspect of the cytidine analogue, for example the low dose of inhaled dry powder 5AZA, is that it is used to achieve improved efficacy over the equivalent inhaled aqueous dose of 5AZA is that the dose could be increased further to reduce tumor growth outside of the lungs.

One aspect of the cytidine analogue inhaled dry powder for example the 5AZA compound and treatment, is that it can be combined with inhibitors of histone deacetylation to further effect tumor growth in the lungs.

One aspect of the cytidine analogue inhaled dry powder, for example the 5AZA compound and treatment, is that it can be combined with inhibitors of histone deacetylation to further effect tumor growth outside of the lungs.

One aspect of the cytidine analogue inhaled dry powder, for example the 5AZA compound and treatment, is that it can be combined with inhibitors of histone methylation to further effect tumor burden in the lungs.

One aspect of the inhaled dry powder cytidine analogue, for example the 5AZA compound and treatment, is that it can be combined with inhibitors of histone methylation to further effect tumor burden outside of the lungs.

Another aspect of one embodiment of the present invention is that addition of a cytidine deaminase inhibitor such as THU increased the plasma C max and AUC for inhaled dry powder cytidine analogue compound supporting a combined use of a cytidine analogue and a cytidine deaminase in treating metastatic lung cancer.

Another aspect of one embodiment of the present invention is that addition of the cytidine deaminase inhibitor THU increased the plasma C max and AUC for inhaled dry powder cytidine analogue compound supporting its combined use with a cytidine analogue such as 5AZA for adjuvant therapy given chronically to cancer patients, for example lung cancer patients following tumor resection to prevent recurrence and improve progression free and overall survival.

Another aspect of one embodiment of the present invention is that addition of the cytidine deaminase inhibitor THU increased the plasma C max and AUC for inhaled dry powder cytidine analogue compound supporting its combined use with a cytidine analogue, for example 5 AZA in epigenetic priming for improving progression free and overall survival when combined with immunotherapy or other therapies that may include chemotherapeutics and small molecule inhibitors.

Another aspect of one embodiment of the present invention is that as compared to inhaled aqueous cytidine analogue compound, the increased efficacy of the inhaled dry powder cytidine analogue for example 5AZA compound for treatment of cancer growing in the lungs support its use in the treatment of other primary tumors that metastasize to the lung that include but, are not limited to breast, colon, and prostate cancer.

Another aspect of one embodiment of the present invention is that as compared to inhaled aqueous cytidine analogue compound, the increased delivery of the inhaled dry powder cytidine analogue, for example the 5AZA compound to the blood, liver, and brain support its use in the treatment of other primary tumor sites that include but are not limited to breast, colon, and prostate cancer.

REFERENCES

1. Chen Z, Fillmore C M, Hammerman P S, Kim C F, and Wong K-K. Non-small cell lung cancers: a heterogenous set of diseases. Nat Rev Cancer 2014; 14:535-56.
2. Siegel, R L, Miller, K D, and Jemal, A. Cancer statistics. C A Cancer J Clin 2017; 67:7-30.
3. Meng X, Liu, Y, Zhang J et al. PD-1/PD-L1 checkpoint blockades in non-small cell lung cancer: New development and challenges. Cancer Lett 2017; 405:29-37.
4. Pao W, Girard N. New driver mutations in non-small cell lung cancer. Lancet Oncol 2011; 12:175-180.
5. Carbone D P, Reck M, Paz-Ares L et al. First-line nivolumab in stage IV or recurrent non-small cell lung cancer. N Eng J Med 2017; 376:2415-2426.
6. Jones P A and Baylin S B. The fundamental role of epigenetic events in cancer. Nat Rev Genet 2002; 3:415-428.
7. Herman J G and Baylin S B. Gene silencing in cancer in association with promoter hypermethylation. N Engl J Med 2003; 349:2042-2054.
8. Nakamura K, Nakabayashi K, Aung K H, Aizawa K, Hori N, Yamauchi J, Hata K, and Tanoue A. DNA methyltransferase inhibitor zebularine induces human cholangiocarcinoma cell death through alteration of DNA methylation status. PLOS One 2015; 10:e0120545.
9. Kantarjian H M, Roboz G J, Kropf P L, Yee K W, O'Connell C L, and Tibes R. Guadecitabine (SG-110) in treatment-naïve patients with acute myeloid leukaemia: phase 2 results from a multicenter, randomized, phase ½ trial. Lancet Oncol. 2017; 18:131T1326.
10. Cameron E E, Bachman K E, Myohanen S, Herman J G, Baylin S B. Synergy of demethylation and histone deacetylase inhibition in the re-expression of genes silenced in cancer. Nat Genet 1999; 21:103-107.
11. Yang A S, Doshi K D, Choi S W, Mason J B, Mamari R K, Gharybian V, Luna R, Rashid A, Shen L, Estecio M R, Kantarjian H M, Garcia-Manero G, and Issa J P. DNA methylation changes after 5-aza-2'-deoxycytidine therapy in patients with leukemia. Cancer Res 2006; 66:5495-5503.
12. Silverman L R, Demakos E P, Peterson B L, Komblith A B, Holland J C, Odchimar-Reissig R, Stone R M, Nelson D, Powell B L, DeCastro C M, Ellerton J, Larson R A, Schifer A, and Holland J F. Randomized controlled trial of azacitidine in patients with the myelodysplastic syndrome: a study of the cancer and leukemia group. J Clin Oncol 2002; 20:2429-40.
13. The Cancer Genome Atlas Research Network. Comprehensive genomic characterization of squamous cell lung cancers. Nature 2012; 489:519-525.
14. The Cancer Genome Atlas Research Network. Comprehensive molecular profiling of lung adenocarcinoma. Nature 2014:511:543-50.
15. Juergens R A, Wrangle J, Vendett B S, Murphy S, Zhao M, Belinsky S A, Herman J G, Baylin S B, Brock M V, and Rudin C M, Combination epigenetic therapy has efficacy in patients with refractory advanced non-small cell lung cancer. Cancer Discovery 2011; 1:598-607.
16. Wrangle J, Wang W, Koch A, Easwaran H, Tsai S, Juergens R A, Topalian S L, Rudin C M, Brock M V, Pardoll D, and Baylin S B. Alterations of immune response of non-small cell lung cancer with azacytidine. Oncotarget 2013; 4:2067-79.
17. Ho D H and Frei E. Clinical pharmacology of 1-beta-darabinofuranosyl cytosine. Clin Pharmacol Ther 1971; 12:944-54.
18. Garcia-Manero G, Bore S D, Cogle C, Ward R, Shi I, Macbeth K J, Laille E, Giordano H, Sakoian S, Jabbour E, Kantarjian H, and Skikne B. Phase I study of oral azacitidine in myelodysplastic syndromes, chronic myelomonocytic leukemia and acute myeloid leukemia. J Clin Oncol 2011; 29:2521-2527.
19. Savona M R, Kokibaba K, Conkling P, Kingsley E C, Becerra C, Morris J C, Rifkin R M, Laille E, Kellerman A, Ukrainskyj S M, Dong Q, and Skikne B S. Extended dosing with CC-486 (oral azacitidine) in patients with myeloid malignancies. Am J Hematol. 2018; 93:1199-1206.
20. Balouzet C, Chanat C, Jobard M, Brandely M-L, and Chast F. Stability of 25 mg/ml azacitidine suspensions kept in fridge after freezing. Pharm Technol Hosp Pharm. 2017; 2:11-16.
21. Handbook of Pharmaceutical Salts: Properties, Selection, and Use. P H Stahl and C G Wermuth (editors) Verlag Helvetica Chimica Acta, Zurich Switzerland, and Wiley-VCH, Weinheim, Germany, 2002.
22. P P Remington. The Science and Practice of Pharmacy, 21$^{st}$ Edition. Lippincott Williams & Wilkins, 2005.
23. R C Rowe, P J Sheskey, and S C Owen. Handbook of Pharmaceutical Excipients 5$^{th}$ Edition. Pharmaceutical Press, 2005.
24. The Pharmaceutical Press and the American Pharmaceutical Association, 2005.
25. Handbook of Pharmaceutical Additives 3$^{rd}$ Addition. M Ash and I Ash (Editors) Gower Publishing Company, 2007.
26. Pharmaceutical and Preformulation and Formulation 2$^{nd}$ Edition. M. Gibson (Editor) CRC Press, 2009.
27. Rajendiran C, Nagarajan P, and Venkateswarlau J. Synthesis of 5-azacytidine. U.S. Pat. No. 9,951,098,098 B2, 2018.
28. March T H, Marron-Terada P G and Belinsky S A. Refinement of an orthotopic lung cancer model in the nude rat. Vet Pathol 2001; 38:483-490.
29. Belinsky S A, Grimes M J, Picchi M A, Mitchell H D, Stidley C A, Tellez C S, Tesfaigzi, Y, Carter, M M, Casero, R A, Baylin, S B, Reed, M D, and March T H. Combination therapy with vidaza and entinostat suppresses tumor growth and reprograms the epigenome in an orthotopic lung cancer model. Cancer Res 2011; 71:454-62.
30. Reed M D, Tellez C S, Grimes M J, Picchi M A, Cheng Y S, March T H, Kuehl P J, and Belinsky S A. Aerosolized 5-azacytidine suppresses tumor growth and reprograms the epigenome in an orthotopic lung cancer model. Br J Cancer 2013; 109:1775-81.
31. Qiu X, Liang Y, Seller R S, Perez-Soler R, and Zou Y. Aerosol azacytidine inhibits orthotopic lung cancers in mice through its DNA demethylation and gene reactivation effects. PLoS One 2014; 9:e109874,
32. Qiu X, Liang Y, Sellers R S, Perez-Soler, R and Zou Y. Toxicity and pharmacokinetic studies of aerosolized clinical grade azacytidine. Olin Lung Cancer 2016; 17:214-222.
33. Gad S C, Cassidy C D, Aubert N, Spainhour B and Robbe H. Nonclinical vehicle use in studies by multiple routes in multiple species. Int J Toxc. 2006' 25:499-521.
34. Lechuga-Ballesteros D, Charan C, Stults C L M, Stevenson, C L, Miller D P, Vehring R, Tep V, and Kuo M-C. Trileucine improves aerosol performance and stability of spray-dried powders for inhalation. J Pharmac Sci. 2008; 97:287-302.
35. Hamishehehkar H, Rahimpour Y, and Javadzadeh Y. The role of carrier in dry powder inhaler. "Recent advances in novel drug carrier systems." INTECH, 2012; Chapter 3:39-66.
36. Wakelle H A, Dahlberg S E, Keller S M, Tester W J et al. Adjuvant chemotherapy with or without bevacizumab in patients with resected non-small cell lung cancer (E1505): an open-label, multicenter, randomized, phase 3 trial. Lancet Oncol. 2017; 18:1610-1623.

What is claimed is:

1. A dry powder pharmaceutical composition suitable for dispersion in an aerosol for inhaled administration to a patient with cancer, the composition comprising:
    a cytidine analogue selected from 5-azacytidine, zebularine, 5-Aza-2'-deoxycitidine, SG-10 or a pharmaceutically acceptable salt, solvate, hydrate, or esters thereof;
    dimethyl sulfoxide (DMSO); and
    a pharmaceutically acceptable excipient;
    wherein the dry powder pharmaceutical composition suitable for dispersion in the aerosol for administration via inhalation to the patient with cancer has a mass median aerodynamic diameter (MMAD) of between about 1.0 um to about 5.0 μm and a geometric standard deviation (GSD) of emitted particle size distribution of the dry powder of about 1.0 um to about 3.4 um.

2. The composition of claim 1 wherein the excipient is an amino acid selected from the group consisting of: leucine, trileucine, isoleucine or any combination thereof.

3. The composition of claim 1 wherein the excipient is a sugar or sugar alcohol.

4. The composition of claim 3 wherein the sugar or sugar alcohol is selected from the group consisting of trehalose, lactose, mannitol, sorbitol, raffinose, inositol and erythritol.

5. The composition of claim 1 wherein the excipient comprises trehalose and/or leucine.

6. The composition of claim 1 wherein the pharmaceutical excipient is from about 99%-1% by weight of the dry powder and wherein the cytidine analogue including salts, solvates, hydrates, and esters thereof is from about 1-99% by weight of the dry powder with between about 0.1-20% residual DMSO.

7. The composition of claim 6 wherein the residual DMSO is between about 5-15% DMSO.

8. The composition of claim 5 comprising:
trehalose in the range of between about 0-99% w/w;
leucine in the range of between about 0-99% w/w;
cytidine analogue and salts, solvates, hydrates, and esters thereof in the range from about 0.1-50%; and
a residual of DMSO between about 0.1-20% residual DMSO.

9. A method of forming the dry powder composition of claim 1 comprising the steps of:
dissolving the cytidine analogue in DMSO to form a cytidine analogue DMSO solution;
dissolving a pharmaceutical excipient in a solvent;
combining the cytidine analogue DMSO solution and the dissolved excipient via mixing;
forming droplets via atomization; and
evaporative drying of the droplets to form particles comprising cytidine analogue having an MMAD of between about 1-5 μm.

10. The method of claim 9 wherein the pharmaceutical excipient comprises an amino acid, a sugar or a combination thereof.

11. The method of claim 10 wherein the amino acid is selected from the group consisting of: leucine, trileucine and isoleucine.

12. The method of claim 10 wherein the sugar is selected from the group consisting of: hexahydric alcohols, and sugar alcohols that include, but are not limited to trehalose, lactose, mannitol, sorbitol, raffinose, inositol and erythritol.

13. The method of claim 9 wherein the pharmaceutical excipient comprises trehalose and/or leucine.

14. The method of claim 9 wherein the dry powder comprises residual DMSO.

15. The method of claim 9 wherein mixing is in-line mixing.

16. The method of claim 9 wherein the cytidine analogue is selected from the group consisting of: 5-azacytidine, zebularine, 5-Aza-2'-deoxycitidine, SG-110 and salts, solvates, hydrates, and esters thereof.

17. The method of claim 9 wherein the pharmaceutical excipient is from about 99%-1% by weight of the dry powder and wherein the cytidine analogue including salts, solvates, hydrates, and esters thereof is from about 1-99% by weight of the dry powder with between about 0-20% residual DMSO.

18. The method of claim 9 wherein the residual DMSO is between about 5-15% DMSO.

19. The method of claim 13 wherein the dry powder composition comprises:
trehalose in the range of between about 0-99% w/w;
leucine in the range of between about 0-99% w/w;
cytidine analogue including salts, solvates, hydrates, and esters thereof in the range from about 0.1-50%; and
a residual of DMSO between about 0.1-20% residual DMSO.

20. The method of claim 9 wherein the composition is formed from atomization of the cytidine analogue in a solution of DMSO.

21. The method of claim 9 wherein the dry powder composition has a MMAD of between about 1-5 μm.

22. A method of treating cancer in a subject comprising:
pulmonary administering to a subject in need thereof a physiologically effective amount of a dispersible pharmaceutical-based dry powder composition of claim 1.

23. The method of treating cancer in a subject of claim 22 wherein the cancer is lung cancer.

24. The method of treating cancer in a subject of claim 22 wherein the cancer is located outside of the lung.

25. The method of claim 22 further comprising:
delivering a therapeutically effective dose of a cytidine analogue compound including salts, solvates, hydrates and esters thereof to the lung of the subject by inhalation of a dispersion formed by aerosolization of a dry powder formulation comprising the cytidine analogue compound at a concentration from about 0.2 to about 10 mg/kg lung dose, wherein a total daily dose of inhaled cytidine analogue compound or derivative thereof does not exceed 1000 mg/kg, and wherein the therapeutically effective dose treats cancer in the subject.

26. The method of claim 25 wherein the aerosolization of the dry powder cytidine analogue compound (i) provides: a mass median aerodynamic diameter (MMAD) of particle size of the dry powder emitted with the aerosolizer of about 0.5 μm to about 5 μm; (ii) provides a Geometric Standard Deviation (GSD) of emitted particle size distribution of the dry powder of about 1.0 um to about 3.4 μm; (iii) provides a fine particle fraction (FPF=% of aerosol particles less than or equal to 5 microns) of particle emitted from the dry powder of at least about 30%;

and (iv) provides an emitted fraction from a device and capsule of at least about 50%.

27. The method of claim 25 wherein a plasma Cmax and/or AUC of the cytidine analogue compound that is obtained after a single inhaled administration of the dry powder aerosolized to the subject is greater than the plasma Cmax and/or AUC of the cytidine analogue compound thereof obtained after a singled inhaled aqueous administration of the cytidine analogue compound nebulized to the subject at a dose that is the same as the dose administered with the inhaled dry powder cytidine analogue compound.

28. The method of claim 25, wherein: a brain Cmax and/or AUC of the cytidine analogue compound that is obtained after a single inhaled administration of the dry powder aerosolized to the subject is greater than the brain Cmax and/or AUC of the cytidine analogue compound obtained after a singled inhaled aqueous administration of an the cytidine analogue compound nebulized to the subject at a dose that is the same as the dose administered with the inhaled dry powder cytidine analogue compound.

29. The method of claim 25, wherein: a liver Cmax and/or AUC of the cytidine analogue compound that is obtained after a single inhaled administration of the dry powder aerosolized to the subject is greater than the liver Cmax and/or AUC of the cytidine analogue compound obtained after a singled inhaled administration of an aqueous cytidine analogue compound nebulized to the subject at a dose that is the same as the dose administered with the inhaled dry powder cytidine analogue compound.

30. The method of claim 25, wherein: a lung Cmax and/or AUC of the cytidine analogue compound that is obtained after a single inhaled administration of the dry powder aerosolized to the subject is greater than the lung Cmax and/or AUC of cytidine analogue compound obtained after a single systemic administration of an aqueous cytidine analogue compound to the subject at a dose that is three fold higher than the dose administered with inhaled dry powder cytidine analogue compound.

31. The method of claim 25 wherein the formulation further comprises an excipient.

32. A pharmaceutical kit comprising an inhalable powder composition comprising:
the inhalable powder composition of claim 1; and
a dry powder inhaler.

33. A container comprising an inhalable powder composition according to claim 1.

* * * * *